United States Patent [19]

Nieminen et al.

[11] Patent Number: 4,819,254

[45] Date of Patent: Apr. 4, 1989

[54] METHOD OF AND APPARATUS FOR RECORDING AND REPRODUCING IMAGE INFORMATION IN PANORAMIC X-RAY PHOTOGRAPHY

[75] Inventors: Timo Nieminen; Tero Nieminen, both of Helsinki, Finland

[73] Assignee: Radiante Oy, Helsinki, Finland

[21] Appl. No.: 5,222

[22] Filed: Jan. 20, 1987

[30] Foreign Application Priority Data

Jan. 23, 1986 [FI] Finland .................................. 8603/21

[51] Int. Cl.$^4$ ........................... A61B 6/00; H05G 1/60
[52] U.S. Cl. ........................................ 378/21; 378/99; 378/38; 378/39
[58] Field of Search ........................ 378/22, 23, 38–40, 378/99, 21

[56] References Cited

U.S. PATENT DOCUMENTS

| | | | |
|---|---|---|---|
| 2,829,263 | 4/1958 | Butler | 378/38 |
| 2,976,416 | 3/1961 | Ellman | 378/38 |
| 4,039,837 | 8/1977 | Ohta et al. | 378/40 |
| 4,145,611 | 3/1979 | Valila | 378/40 |
| 4,239,971 | 12/1980 | Cushman | 378/39 |
| 4,263,513 | 4/1981 | Palluck | 250/439 |
| 4,589,122 | 5/1986 | Nicminen | 378/39 |
| 4,683,581 | 7/1987 | Tammisalo et al. | 378/38 |

FOREIGN PATENT DOCUMENTS 3037478 3/1980 Fed. Rep. of Germany .

OTHER PUBLICATIONS

Paatero, Y. V., "Parablograf:," *Suomi hammaslaak. toim.* 90, (1949)—With English Summary.

*Primary Examiner*—Carolyn E. Fields
*Assistant Examiner*—John C. Freeman
*Attorney, Agent, or Firm*—Morse, Altman, Dacey & Benson

[57] ABSTRACT

The invention relates to a method of and an apparatus for recording image information in panoramic X-ray photography. The total information contained in a beam of X-rays penetrated through an object is recorded on a memory disc, whose configuration is substantially the same as that of an object to be imaged, such as a dental arch, said memory disc being kept stationary during the filming relative to the object to be imaged. The memory disc is used for producing or presenting layerwise reproduced images of desired layers. The preparation of reproduced images from the memory disc can be performed on a principle corresponding to conventional panoramic tomography with the exception that the object to be imaged is a memory disc.

8 Claims, 6 Drawing Sheets

METHOD OF AND APPARATUS FOR RECORDING AND REPRODUCING IMAGE INFORMATION IN PANORAMIC X-RAY PHOTOGRAPHY

The present invention relates to a method of and apparatus for recording and reproducing image information in panoramic X-ray photography, wherein a beam of X-rays penetrating through an object to be imaged is scanned over a section to be imaged in said object and the information representing a desired layer in the object is picked up from the total information produced by a beam of rays penetrated through the object.

This type of panoramic photography is employed e.g. in imaging or filming a dental arch. One example of such apparatus is disclosed in U.S. Pat. No. 4,263,513 and another example in U.S. Pat. No. 4,589,122.

DETAILED DESCRIPTION OF THE PREFERRED EMBODIMENTS

Prior to describing the solution of this invention, the essential theory of panoramic photography will be explained with reference made to the accompanying FIGS. 1–4.

Let us presume that an object to be filmed spins around point 0 at the moment of observation. A narrow beam of rays emitting from the focus F of an X-ray tube projects e.g. a target point K on its centre axis to point P on a level to be examined, an image level T.

If a target point K moves downwards in the figure at a velocity $v_k$, the projection point P moves also downwards but, due to a greater distance from the projection focus F, at a higher velocity $v_p$. Examination of the figure leads to $$\frac{v_p}{v_k} = \frac{l_p}{l_k}$$

This leads further to $$v_p = \frac{l_p}{l_k} v_k$$

If a film is placed on image level T and given a velocity $$v_p = v_{p'}$$

a sharp image of target point K is obtained on the film.

The points further away from spinning centre 0 are moving faster than the film and become blurred. On the other hand, the nearest points move slower than the film and are also blurred. The points imaging with acceptable sharpness define a so-called imaging layer, visible in this FIG. 1.

Figure 2:
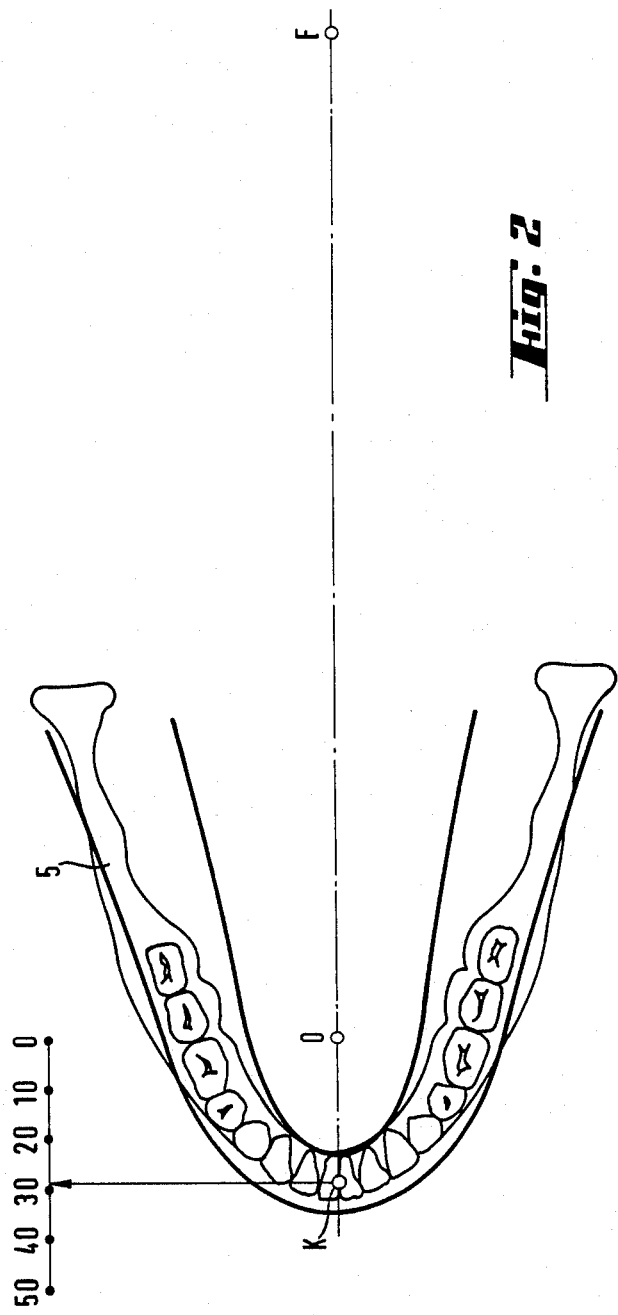
FIGS. 2–4 are views similar to FIG. 1 but illustrating a dental arch in various positions therein.

By placing an object, as a jaw in the case of FIG. 2, within the imaging layer, a sharp image is produced thereof.

Figure 3:
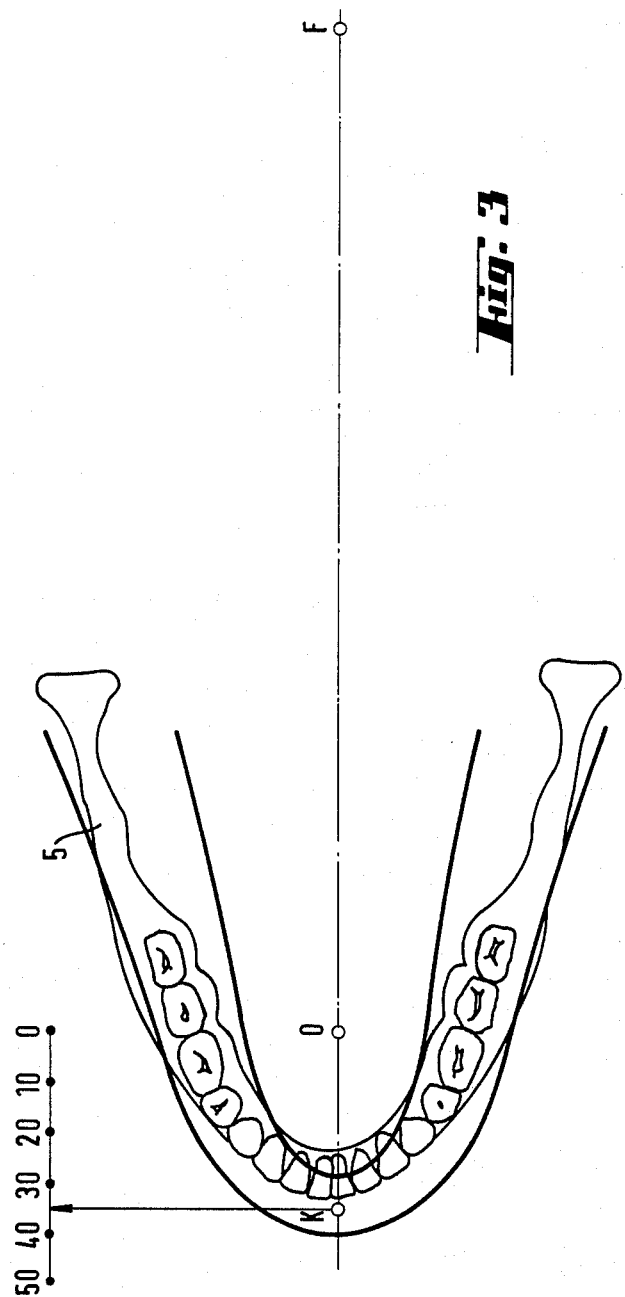
Figure 4:
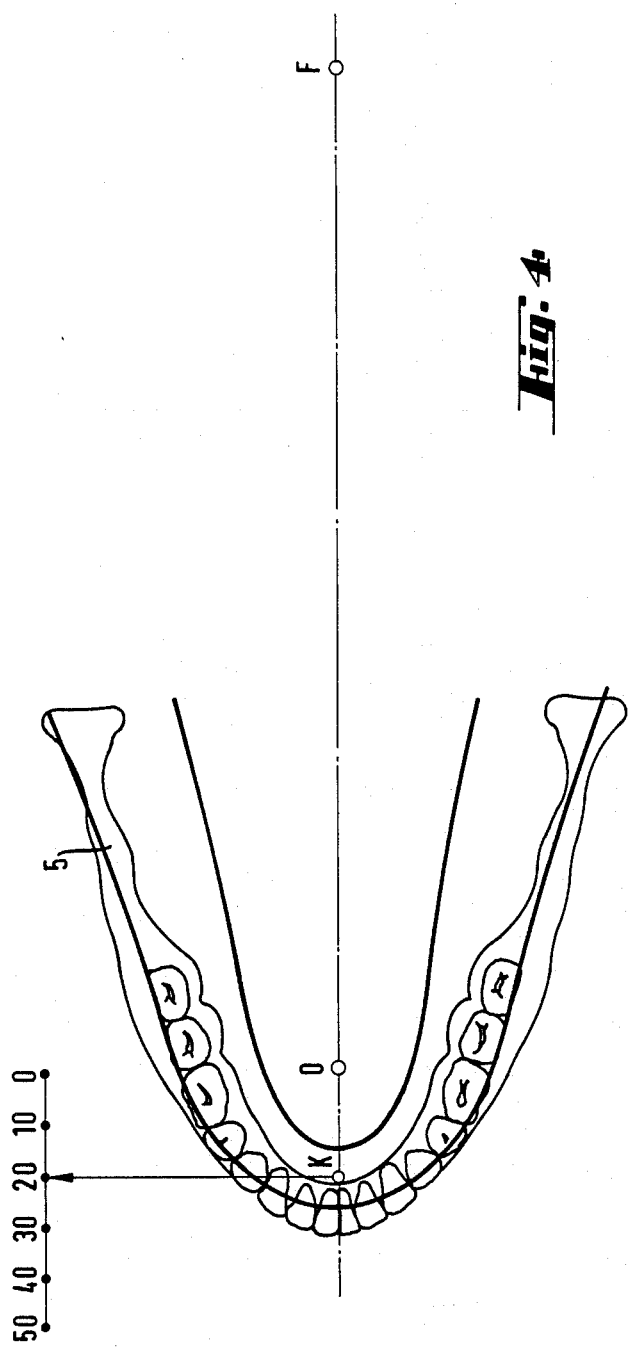

In addition to the above, it is known that if a film cassette is given one way or another a velocity higher than the one just described, the imaging layer moves further away from focus F, which has happened in FIG. 3. On the other hand, a lower velocity moves the imaging layer closer to focus F. This is shown in FIG. 4.

The possibility of varying the velocity can be used e.g. for accurately positioning an imaging layer without moving a patient. This has been done in some devices.

If an object to be filmed does not for some reason find itself in an imaging layer, a filming must be repeated by moving the imaging layer in a patient. This leads to several drawbacks and furthermore to the increase of a necessary radiation dosage.

An object of the invention is to provide a method of and apparatus for recording and reproducing image information in panoramic filming in a manner that the recorded image information can be used to produce new images of desired layers without having to re-film the actual object to be filmed.

This object is achieved by means of a method of the invention in a manner that the total information of a beam of rays penetrated through an object is recorded on a memory disc and the memory disc is used to produce or present layerwise images of desired layers. During the filming, the memory disc is kept stationary relative to an object being filmed.

The preparation of layerwise images from a memory disc can be performed in several ways, some examples of which are described next. One way is to apply a principle corresponding to conventional panoramic tomography, but this time the filmed object is a memory disc which contains the same total information as that contained in the radiation penetrated through a filmed object. If the employed memory disc is a film, the images corresponding to a desired layer or section can be picked up with the light showing from the film. The light that has penetrated the film contains the same total information as the beam of rays penetrated through a filmed object and, hence, by selecting the relative speed of a beam of light scanning the film and that of a film used for re-filming in a desired manner, a desired section can be re-filmed.

When using a method and apparatus of the invention, the reproduction of an image need not be associated with the actual filming apparatus but, instead, it is possible to employ a separate image reproduction apparatus, into which is inserted a memory disc provided with total image information. In the image reproduction apparatus, an image corresponding to a certain section is picked up from the total information of a memory disc onto a film or a display screen by inducing a speed difference between a memory disc pick-up scan and an image output or display scan. Reproduction of an image on a film can be carried out in a manner that the output film of a tomogram is exposed through a memory disc by means of a narrow beam of light scanning over the memory disc and output film while, at the same time, a speed difference in the direction of scan is induced on the output film and memory disc, said speed difference defining a section to be picked up from a memory disc. However, if an image is reproduced on a display screen, the memory disc is filmed with a video camera and the scanning speed of the line of a display screen is adjusted by adjusting the width of said image for picking up a desired section from the memory disc. To put it briefly, in each case the width of a reproduced image is slightly narrower than that of the total information contained in a memory disc, said difference in widths corresponding to the above-mentioned speed difference between the pick-up scan from a memory disc and the output or display scan of a tomogram.

In a display screen application, an object can be examined from different depths, like section by section. This way it is possible to locate a desired section or sections for re-filming. Thus, it is practical to combine the image reproduction occurring on a film and on a display screen in a manner that the search of a section is effected on a screen followed by photographing the desired section on a film.

Figure 5:
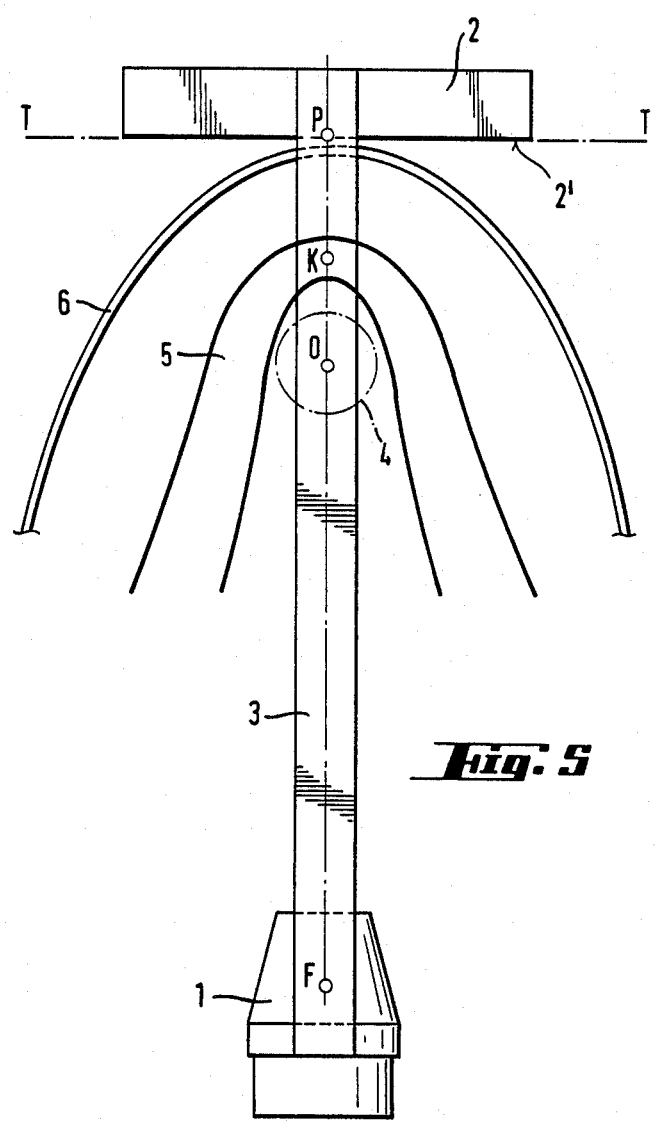
FIG. 5 is a schematic plan view of an imaging apparatus according to the invention.
Figure 6:
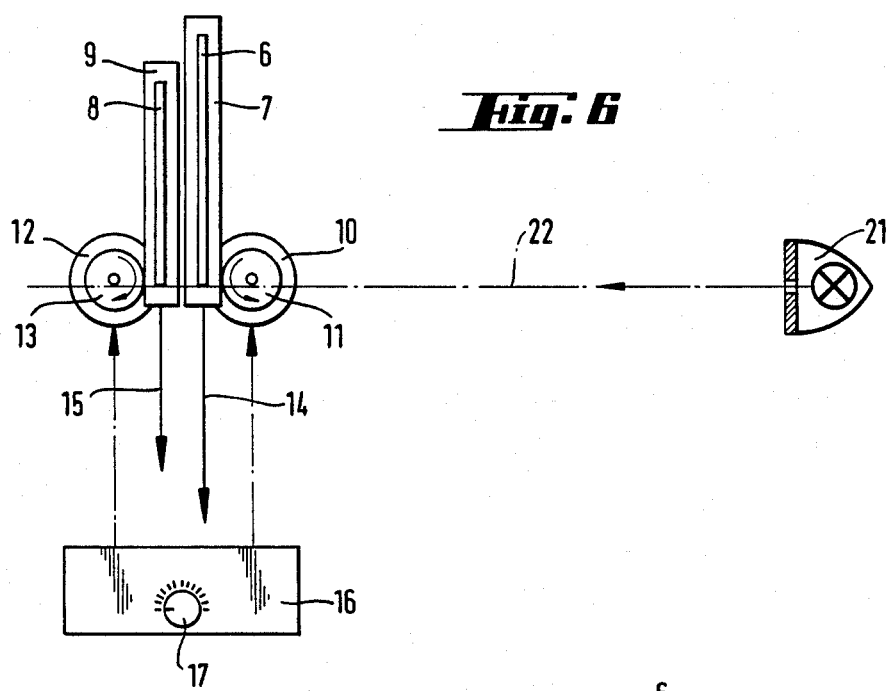
FIG. 6 is a schematic side elevation of an image reproduction device according to the invention.
Figure 7:
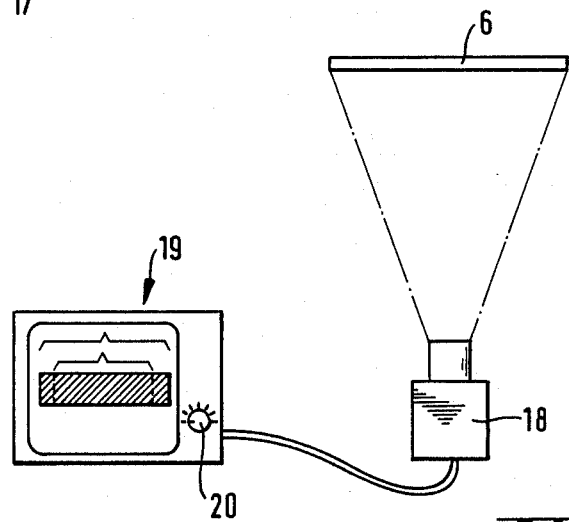
FIG. 7 is a schematic side elevation of another image reproduction device according to the invention.

The invention will now be described in more detail with reference made to the embodiments shown in FIGS. 5-7. FIG. 5 is a schematical plan view of one embodiment of the invention. FIG. 6 shows diagrammatically an image reproduction device, which is separate from the filming apparatus. FIG. 7 shows diagrammatically another image reproduction device, which is also separate from the filming apparatus.

Figure 1:
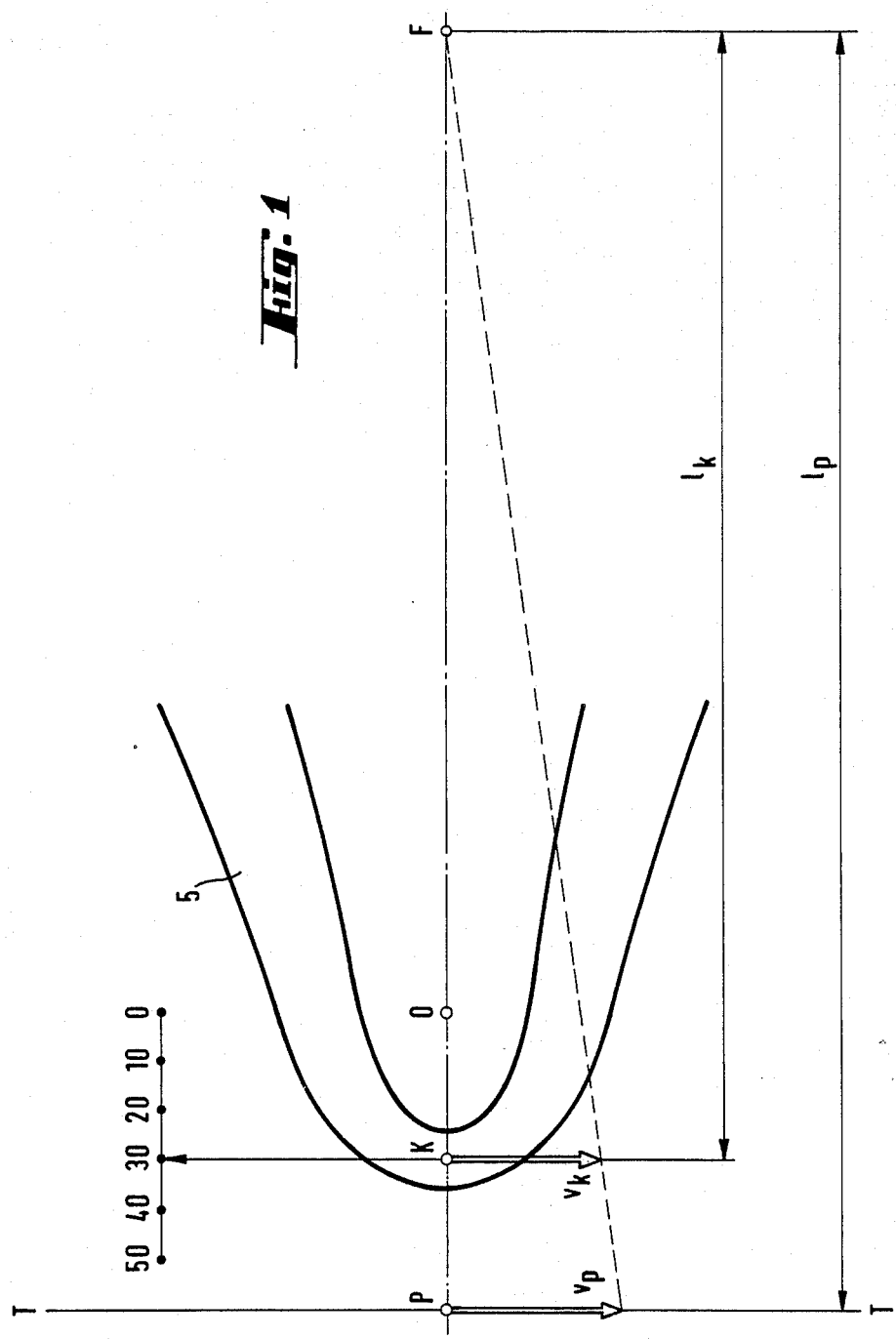
FIG. 1 is a diagram helpful in understanding the invention.

In FIG. 5, points F, O, K and P correspond to the points designated by the same letters in FIG. 1. An X-raysource 1 and a film-carrying cassette 2 are mounted on the opposite ends of a handle 3. Handle 3 is rotatable around an axis O by means of any drive means 4. The object to be filmed is a dental arch 5. The pivot axis O can be movable relative to the filmed object 5, as desired, and/or said handle 3 can be movable relative to axis O and/or said cassette 2 can be movable relative to handle 3 and even a film 2' can be movable relative to cassette 2. Putting the invention into practice is in no way dependable on the prior known relative movements of these prior known components. By means of these prior known components, the filming is effected in a manner that the piece of information illustrating a desired section is "picked up" at a suitable speed of cassette 2 from the total information coming onto a film 2' through the filmed object 5 with the help of a beam of rays.

The basis of this invention is a realization that, in addition to or instead of said piece of information, there is recorded said total radiation information and this record can be later used for picking up the piece of information for re-filming. This is why, in the case of FIG. 5, between a filmed object 5 and a film cassette 2 is placed a memory disc 6, whose configuration substantially corresponds to the curved shape of a dental arch to be filmed. Memory disc 6 is stationary relative to the filmed object 5. During the imaging spin movement around said axis O, all the information is recorded on memory disc 6 which is offered by a beam of rays for a film 2'. From the total information recorded on memory disc 6 it is later possible to pick up various sections (without re-filming a patient).

In applying conventional technology, it is conceivable that the memory disc 6 is a film, from which images are reproduced on a principle corresponding to the above-described panoramic photography with a difference, however, that the filmed object is a memory disc film and the filming can be effected e.g. by using visible light.

Since a memory disc can be attached any time to a panoramic filming apparatus, an essential part of the invention is a separate image reproduction device for picking up tomograms from the total image information contained on a memory disc.

FIG. 6 depicts an image reproduction device separate from the imaging apparatus of FIG. 5. In this case, the memory disc 6 provided with the total image information is placed in a holder 7, movable by means of a motor 10 and a friction wheel 11 at a certain speed in the direction of an arrow 14. A source of light 21 is used to direct a narrow beam of light 22 across the travel path of the memory disc 6. Behind memory disc 6 is positioned an output film 8 in a holder 9 which a motor 12 moves by means of a friction wheel 13 in the direction of an arrow 15. In the direction of travel, said output film 8 is narrower than memory disc 6 and output film 8 is set to move at a velocity lower than memory disc 6. Due to the speed difference, the information corresponding only to a certain section is exposed as a sharp image on the output film 8 from that total information which a beam of light rays 22 picks up from memory disc 6. The speed of motors 10 and 12 can be controlled by means of a control device 16 and the speed difference is adjusted by means of a regulating device 17.

In the embodiment of FIG. 7, the memory disc 6 is photographed with a video camera 18 and the image is shown on a display screen 19. In a normal situation, the display screen 19 only shows the total information image of memory disc 6, said image being indefinite and not defining any particular section. As a regulator 20 is used to adjust the width of the image on display screen 19, in other words the line scanning velocity is adjusted, a desired section is brought to be visible on screen 19. The image width regulator 20 can be used to examine an object from different depths section by section.

The devices shown in FIGS. 6 and 7 can be calibrated for co-operation in a manner that the same position of regulators 20 and 17 represents the reproduction of one and the same layer. The devices 6 and 7 can of course be combined in the same apparatus, in which case said memory disc 6 needs to be placed in its holder only once. First, said display screen and its control means are operated to find a desired image layer, followed by recording said image layer on a film 8.

In order to facilitate the co-operation and coordination between the devices shown in FIGS. 6 and 7 so that an identical position of the regulators or control means 20 and 17 represents in both cases the reproduction of one and the same desired layer, the two devices preferably are calibrated. The calibration is in the form in which each of the control means 20, and 17 is provided with a scale, as represented by the spokes above the respective circles representing the respective regulators 17 and 20, for visually comparing and manually transferring an adjustment reading corresponding to the same layer from one control means 20 to the other control means 17 by manually positioning the control means 17 to the corresponding adjustment reading of the scale of control means 20.

It is obvious that modern technology offers practically unlimited possibilities regarding the physical construction and possible applications of a memory disc. The recording of image information can also be effected by utilizing computer technology.

The above object of application and embodiment are only intended for illustrating and by no means for limiting the invention, since the applications and the practical designs of a method of the invention may vary in many ways within the scope of the annexed claims.

What is claimed is:

1. A method of recording total information and reproducing layerwise images thereof in panoramic x-ray photography comprising:
   (a) exposing an object to be imaged to a beam of x-rays;
   (b) recording the total information of said x-rays penetrated through said object on a photographic disc;
   (c) using said photographic disc to produce layerwise images of desired layers of said object; and
   (d) producing an image, corresponding to a certain layer of said desired layers from said total information recorded on said photographic disc, recorded from said photographic disc onto a display screen via a camera or directly recorded from said photographic disc onto a film by inducing a speed difference during said producing between a pick-up scan of said photographic disc and an image output on said tomogram film or on image output on said display screen.

2. A method of recording total information and reproducing layerwise images thereof in panoramic x-ray photography comprising:
   (a) exposing an object to be imaged to a beam of x-rays;
   (b) recording the total information of said x-rays penetrated through said object on a photographic disc; and
   (c) using said photographic disc to produce layerwise images of desired layers of said object,
   (d) wherein said production of said layerwise images of desired layers of said object is produced by using a beam of light to pick up said layerwise images from said photographic disc.

3. The method of claim 1 wherein said photographic disc is first used in an imaging apparatus for recording said total information thereon and is then used in an image reproduction device separate from said imaging apparatus, in said image reproduction device an image, corresponding to a certain layer of said desired layers from said total information recorded on said photographic disc, is recorded from said photographic disc onto a display screen via a camera or is directly recorded from said photographic disc onto a film by inducing a speed difference during said recording between a pick-up scan of said photographic disc and an image output on said film or an image output on said display screen.

4. The method of claims 1 or 3 wherein said photographic disc is a film from which said layerwise images are recorded by means of visible light.

5. The method of claim 4 further characterized in that said film is a tomogram output film which is exposed through said photographic disc with a narrow beam of light 22 scanning over said photographic disc and said tomogram output film, and including inducing a speed difference in the direction of and during said scanning between said photographic disc and said tomogram output film for the determination of a layer of said desired layers of said object 5 to be recorded on said tomogram output film from said photographic disc.

6. The method of claims 1 or 2 further characterized in that said photographic disc is viewed with a video camera, with the line scanning speed of a tomogram display screen being controlled by adjusting the width of an image for picking up a desired layer of said object from said photographic disc.

7. An apparatus for recording total information and reproducing layerwise images thereof in panoramic x-ray photography comprising:
   (a) support means supporting a source of x-rays at one end of said support means and an image recording means at the other end of said support means;
   (b) drive means for moving said source of x-rays relative to an object to be imaged by a beam of x-rays emanating from said source;
   (c) said image recording means including a photographic disc stationarily mounted relative to said object, said photographic disc recording the total information of said beam of x-rays penetrated through said object;
   (d) means for producing an image corresponding to desired layer selectively from said total information recorded on said photographic disc; and
   (e) an image reproduction device separate from said apparatus and including said means for producing said image from said total information recorded on said photographic disc, said image reproduction device further comprising means for recording said desired layer directly from said photographic disc onto an output film or means for recording said desired layer from said photographic disc onto a display screen via a camera and further comprising film control means or display control means for effecting a speed difference between the recording scan of said photographic disc and an image output on said film or a display scan on said display screen.

8. The apparatus of claim 7 further including a scale on said control means for visually comparing and manually transferring an adjustment reading corresponding to said desired layer to the control means.

* * * * *